US008268864B2

(12) United States Patent
Fyrnys et al.

(10) Patent No.: US 8,268,864 B2
(45) Date of Patent: Sep. 18, 2012

(54) COMBINATION OF ANTICHOLINERGICS AND LEUKOTRIENE RECEPTOR ANTAGONISTS FOR THE TREATMENT OF RESPIRATORY DISEASES

(75) Inventors: Beatrix Fyrnys, Muhlheim (DE); Torsten Hoffmann, Radebeul (DE); Mario Weingart, Dresden (DE); Istvan Szelenyi, Schwaig (DE); Peter Jurgen Cnota, Bad Homburg (DE); Ullrich Munzel, Wollstadt (DE); Ursula Petzold, Bickenbach (DE); Joachim Maus, Muhlheim (DE)

(73) Assignee: Meda Pharma GmbH & Co. KG, Bad Homburg (DE)

( * ) Notice: Subject to any disclaimer, the term of this patent is extended or adjusted under 35 U.S.C. 154(b) by 1132 days.

(21) Appl. No.: 11/376,615

(22) Filed: Mar. 16, 2006

(65) Prior Publication Data

US 2006/0211729 A1    Sep. 21, 2006

Related U.S. Application Data

(60) Provisional application No. 60/661,918, filed on Mar. 16, 2005.

(51) Int. Cl.
*A01N 43/42* (2006.01)
*A01N 43/36* (2006.01)
*A61K 31/47* (2006.01)
*A61K 31/40* (2006.01)
*C07D 207/00* (2006.01)
*C07D 453/04* (2006.01)

(52) U.S. Cl. ......... 514/311; 514/424; 548/541; 546/134
(58) Field of Classification Search .................. 514/311, 514/424; 548/541; 546/134
See application file for complete search history.

(56) References Cited

U.S. PATENT DOCUMENTS

| 5,712,298 | A | 1/1998 | Amschler et al. |
| 6,086,914 | A * | 7/2000 | Weinstein et al. ............. 424/451 |
| 6,204,285 | B1 | 3/2001 | Fabiano et al. |
| 6,384,038 | B1 * | 5/2002 | Rubin ...................... 514/255.04 |
| 6,475,467 | B1 | 11/2002 | Keller et al. |
| 6,645,466 | B1 | 11/2003 | Keller et al. |
| 7,258,118 | B2 | 8/2007 | Goede et al. |
| 2001/0025040 | A1 * | 9/2001 | Poppe et al. ............. 514/217.05 |
| 2001/0027789 | A1 | 10/2001 | Goede et al. |
| 2002/0115681 | A1 | 8/2002 | Bozung et al. |
| 2002/0151597 | A1 | 10/2002 | Banerjee et al. |
| 2003/0068280 | A1 | 4/2003 | Bannister et al. |
| 2003/0119802 | A1 | 6/2003 | Gavin |
| 2004/0002548 | A1 | 1/2004 | Bozung et al. |
| 2004/0028734 | A1 | 2/2004 | Bannister et al. |
| 2004/0038958 | A1 | 2/2004 | Rundfeldt et al. |
| 2004/0053902 | A1 * | 3/2004 | Smith ........................... 514/171 |
| 2005/0288265 | A1 | 12/2005 | Locher et al. |
| 2006/0081246 | A1 | 4/2006 | Goede et al. |
| 2006/0147382 | A1 | 7/2006 | Bundschuh et al. |

FOREIGN PATENT DOCUMENTS

| EP | 1449528 | 8/2004 |
| WO | WO-01/76575 | 10/2001 |
| WO | WO-02/069945 | 9/2002 |
| WO | WO-02078671 | 10/2002 |
| WO | WO-02/096423 | 12/2002 |
| WO | WO-02/096463 | 12/2002 |
| WO | WO-03/011274 | 2/2003 |
| WO | WO-2004019984 | 3/2004 |
| WO | WO-2005/055999 | 6/2005 |

OTHER PUBLICATIONS

Herbst et al. "Selective oral epidermal growth gactor receptor tyrosine kinase inhibitor zD1839 is generally well-tolerated and has activity in non-small-cell lung canger and other solid tumors: results of a Phase I trial" Journal of Clinical Oncology, Sep. 15, 2002, vol. 20, No. 18, pp. 3815-3825.*
Mueller et al. "Development of a powder for inhalation with R,R-glycopyrrolate as active ingredient for the delivery from novel multidose dry powder inhaler" European Respiratory Society Annual Congress 2003, Sep. 27, 2003, abstract 2977.*
Finsnes et al. "Leukotriene antogonism reduces the generation of endothelin-I and interferon-gamma and inhibits eosinophili airway inflammation" Respiratory Medicine, 2002, vol. 96, pp. 901-906.*
Reid P., "Roflumilast", Current Opinion in Investigational Drugs, Current Drugs, London, GB, vol. 3, No. 8, Aug. 2002, pp. 1165-1170, XP001119630, ISSN: 0967-8298 Abstract.
Santing et al., "Phosphodiesterase inhibitors reduce bronchial hyper-reactivity and airway inflammation in unrestrained guinea pigs", European Journal of Pharmacology, vol. 275, No. 1, pp. 75-82 (Feb. 4, 1992).
International Search Report dated Nov. 23, 2005, issued in PCT/EP2005/000649.
Pahl, Andreas, Possible Synergistic Effects f R.S/S,R-glycopyrolate and Tiotroplum with the Glucocorticoid Budesonide, Viatris; No. 2006-03, Jul. 19, 2006.
Austen et al. at p. 856 (Austen et al. Samter's Immulogic Diseases. Philadelphia: Lippincott Williams & Wilkins, 2001.
Brostoff et al. Clinical Immunology. London: Gower Medical Publishing, 1991.
Gennaro, Alfonso. Remington's: Pharmaceutical Sciences. Easton, PA: Mack Publishing Co., 1985.
Roitt et al., Immunology. $3^{rd}$ Ed. St. Louis: Mosby, 1993.

* cited by examiner

*Primary Examiner* — Sreeni Padmanabhan
*Assistant Examiner* — Kendra D Carter
(74) *Attorney, Agent, or Firm* — Venable LLP; Keith G. Haddaway

(57) ABSTRACT

Pharmaceutical compositions comprising an anticholinergic and at least one leukotriene inhibitor for treatment of respiratory diseases, including allergic rhinitis, bronchial asthma, COPD and common cold, and methods of treatment.

17 Claims, No Drawings

COMBINATION OF ANTICHOLINERGICS AND LEUKOTRIENE RECEPTOR ANTAGONISTS FOR THE TREATMENT OF RESPIRATORY DISEASES

CROSS-REFERENCE TO RELATED APPLICATIONS

This application claims priority to U.S. provisional application No. 60/661,918, filed Mar. 16, 2005, which is incorporated herein by reference in its entirety.

FIELD OF THE INVENTION

The present invention relates to a combination comprising topical (inhaled) anticholinergics and inhaled or oral leukotriene (LT) receptor antagonists (BLT- and CysLT-receptor antagonists) for the treatment of respiratory diseases including allergic rhinitis, bronchial asthma and chronic obstructive pulmonary diseases (COPD). It further comprises the presentation of this combination in a locally applied (inhaled) formulation and application in an inhalation device for instance in the Novolizer®.

BACKGROUND

Allergic rhinitis affects 20% of the adult population and up to 40% of children. Although rhinitis itself is not life threatening (unless accompanied by severe asthma or anaphylaxis), morbidity from the condition can be significant. Allergic rhinitis often coexists with other disorders, such as asthma, sinusitis, nasal polyps, allergic conjunctivitis, and atopic dermatitis. Rhinitis may also considerably reduce quality of life, productivity, learning, etc. Furthermore, insufficient therapy of rhinitis may lead to other disorders including infection of the sinuses, ears and lower respiratory tract. Effective therapy for allergic rhinitis requires understanding the pathophysiology of the disease, as well as the role of various inflammatory mechanisms. As such, various classes of medication are at the physicians' disposal to treat patients with allergic rhinitis. Among these are $2^{nd}$ generation antihistamines and anticholinergic agents, intranasal corticosteroids, and mast cell stabilizers. Recently, leukotriene (LT) receptor antagonists have been added to the modes of therapy.

The mechanism of allergic rhinitis is a typical allergic disease. With regard to its pathophysiology, there are several similarities between rhinitis and asthma. Rhinitis is defined as inflammation of the nasal membranes and is characterized by a symptom complex that consists of any combination of the following: sneezing, nasal congestion, nasal itching, and rhinorrhea. To date, histamine $H_1$-receptor antagonists, decongestants, sodium cromoglycate, corticosteroids, cysLT-receptor antagonists and anticholinergics are most commonly used pharmacological agents for the treatment of rhinitis.

Asthma bronchiale, affecting as many as 10% of individuals in industrialized nations, is characterized by bronchoconstriction, chronic airway inflammation, airway hyperreactivity, and mucosal oedema. Airway remodelling and altered non-cholinergic, nonadrenergic neurotransmission may contribute to irreversible airway obstruction and reduction of pulmonary function. Asthma bronchiale has emerged as a major public health problem worldwide over the past 20 years. Although data indicate that current asthma therapies led to limited decreases in death rates, it continues to be a significant health care problem. It still is one of the leading causes of preventable hospitalization worldwide and accounts for several million lost workdays. Along with the increase in asthma prevalence, the costs associated with this disease have also risen dramatically.

The pathophysiology of asthma involves an intricate network of molecular and cellular interactions, although the contribution of each individual factor is probably different from patient to patient depending on the setting and stimulus. Major participants in the development of an asthma phenotype include the triggering stimuli such as the allergens themselves, cells such as T cells, epithelial cells and mast cells that produce a variety of cytokines including IL-5, GM-CSF, IL-3, IL-4 and IL-13 and chemokines such as eotaxin, adhesion molecules, etc. Recent advances in understanding the inflammatory and immunological mechanisms of asthma have indicated many potential therapeutic avenues that may prevent or reverse abnormalities that underlie asthma.

At present, pharmacotherapy is the mainstay of treatment of asthma. Short- and long-acting inhaled $\beta_2$-adrenoceptor agonists are available. The short-acting $\beta_2$-adrenoceptor agonists are now used on an on-demand-basis for rapid relief of symptoms. In recent years, long-acting inhaled $\beta_2$-adrenoceptor agonists have had an increasing role in the management of asthma, particularly in patients with moderate to severe asthma. Antimuscarinic drugs are rather less efficacious in the relief of an asthma attack than the $\beta_2$-adrenoceptor agonists (Rodrigo and Rodrigo, Chest 2002; 121:1977-87). However, with the introduction of the new anticholinergic tiotropium, the use of anticholinergics in respiratory diseases will enormously increase. Inhaled corticosteroids have become the mainstay of therapy in chronic asthma. They are the most clinically effective treatment available but can produce serious secondary effects and, moreover, be inefficient in corticosteroid-resistant asthmatics.

Chronic obstructive pulmonary disease (COPD) is also very common. This disease is characterized by a progressive airflow limitation accompanied by inflammatory reactions. From a review of data from all over the world, it is clear that tobacco is not the only cause of COPD. The worldwide increasing age is also a certain risk factor. The prevalence of COPD varies between 3% and 10% with a steadily increasing trend. Although COPD is a leading cause of illness and death, its recognition as a public health problem has been slow to evolve despite the rising mortality rate for COPD and the decline in death rates for most of the cardiovascular diseases (Hurd Chest 2000; 117(2 Suppl):1S-4S). Additionally, COPD imparts substantial economic burden to individuals and society.

In general, much less is known about the pathogenesis of COPD than that of asthma. Recent studies have greatly expanded the understanding of pathogenetic mechanisms underlying COPD. Thus, there is consent that COPD is also an inflammatory disease. From the present pathogenetical point of view, neutrophil granulocytes, CD8+ lymphocytes and macrophages with their mediators probably play crucial roles in the pathogenesis of COPD.

The current management is focussed on the improvement of the lung function of patients suffering from COPD. The first step is in this process smoking cessation. There is evidence that smoking reduction or cessation may result in improvement of some respiratory parameters. Bronchodilators ($\beta_2$-adrenoceptor agonists and anticholinergics) are now the mainstay of symptomatic therapy. Short- and long-acting $\beta_2$-adrenoceptor agonists such as salbutamol, fenoterol, salmeterol, formoterol are established therapeutics in the symptomatic COPD management. Of the short-acting antimuscarinic drugs, ipratropium is widely used. Recently, tiotropium, a long-acting anticholinergic with a certain preference to $M_3$-muscarinic receptors has now been introduced worldwide (Hansel and Barnes, Drugs Today (Barc) 2002; 38:585-600). Anticholinergic agents can effectively be used in the treatment of COPD in horses, as well. Ipratropium at a dose of 2,400 µg/horse is an effective bronchodilator in horses with COPD (Duvivier et al. Equine Vet J 1999; 31:20-4, Bayly et al. Equine Vet J. 2002 Jan; 34(1):36-43). At present, the anti-inflammatory therapy of COPD is unsolved. The use of systemic and inhaled glucocorticoids for COPD has increased appreciably over the past 20 years. They have been tested on the premise that interference with inflammation in COPD should alter the course of the disease. Although inhaled corticosteroids have a proven benefit in the management of asthma, but until recently, their efficacy in non-asthmatic, smoking-related COPD was not evidence-based (Bonay et al. Drug Saf 2002; 25:57-71). Inhaled corticosteroids have relatively little impact on the inflammatory processes that characterize COPD (Adcock and Chung, Curr Opin Investig Drugs 2002; 3:58-60).

Airflow obstruction and airway inflammation are features of allergic rhinitis/asthma as well as COPD. There is strong evidence that airway inflammation is a predominant underlying problem in patients with rhinitis, asthma and COPD. Although the airway inflammation in rhinitis/asthma and COPD, respectively, involve different cell types, both diseases are of chronic inflammatory nature associated with cellular infiltration and activation. While allergic rhinitis and bronchial asthma is predominantly characterized by eosinophils and CD4 lymphocytes, neutrophil granulocytes, CD8 lymphocytes and macrophages appear to play a major role in the pathogenesis of COPD.

Asthma- and COPD-like diseases, respectively, can also occur in animals, e.g. in horses. There is evidence that $LTB_4$ and $LTD_4$ could contribute to the pathogenesis of equine COPD (Marr et al. Res Vet Sci 1998; 64:219-24). In horses, there is apparently a link between LTs generation and the cholinergic system. Neutrophilic inflammation in the airways and bronchospasm mediated via muscarinic receptors are features of COPD in horses. LTs are reported to be involved in the exacerbation of COPD. Indeed, mediators such as LTs augment the cholinergic response in equine airways (Olszewski et al. Am J Physiol 1999; 276:L522-9). There is also evidence that cholinergic activation (acetylcholine) stimulates alveolar macrophages to release lipoxygenase-derived products (LTB4 and CysLTs) (Sato et al. Am J Physiol 1998; 274:L970-9).

Rhinoviruses are the cause of more than 50% of respiratory tract infections. Complications of rhinovirus infections (e.g. common cold), which include for example the manifestation or exacerbations of asthma, can be significant in certain populations. Therefore, it may be of great advantage to minimize the potential adverse consequences by using an adequate therapy. Recently it has been demonstrated that rhinovirus colds induce bronchial inflammation with markedly enhanced expression of 5-LO pathway proteins (Seymour et al J Infect Dis 2002; 185:5404) indicating that the production of LTs in these airway is augmented. Consequently, LT antagonists appear to be able to reduce lung symptoms subsequent to virus infection (Bisgaard et al. Am J Respir Crit Care Med 2003; 167:379-83). Furthermore, it is well known that anticholinergics like ipratropium provide specific relief of rhinorrhea and sneezing associated with common colds (Hayden et al. Ann Intern Med 1996; 125:89-97).

Leukotrienes (LTs) are important mediators of the pathophysiology of allergic airway diseases such as asthma and rhinitis, and they are also involved in COPD. The main effects mediated via LTS are bronchoconstriction, airway inflammation, oedema and mucus hypersecretion.

Arachidonic acid metabolism via 5-lipoxygenase results in a group of biologically active lipids known as leukotrienes (LTs). $LTB_4$ is a potent activator of leukocyte chemotaxis. Cysteinyl LTs ($LTC_4$, $LTD_4$, $LTE_4$) account for the spasmogenic activity previously described as slow-reacting substance of anaphylaxis (SRS-A). These inflammatory mediators are produced by a number of cell types including mast cells, neutrophils, eosinophils, basophils, macrophages and monocytes. They exert their biological effects by binding and activating specific receptors ($LTB_4$ at the BLT receptor, cysteinyl-LTs at the $cysLT_1$-receptor). This occurs in a series of events that lead to contraction of the human airway smooth muscle, chemotaxis and increased vascular permeability, mucus hypersecretion, decrease of ciliary motility. These effects have led to their important role in the diseases of asthma, allergic rhinitis and COPD.

CysLT-receptor antagonists (e.g. zafirlukast, montelukast, pranlukast) derivatives of other LT-receptor antagonists, such as L-648,051, MK-571, verlukast (MK-0679), pobilukast (SK&F 104353), AS-35, ICI 204,219, etc.) represent an effective and well-tolerated treatment for asthma and allergic rhinitis in adults and children, particularly for exercise- and aspirin-induced asthma. They can also have clinical applications in the COPD. Recently, it has been suggested that zafirlukast, a cysLT-receptor antagonist may increase the tidal volume and alveolar ventilation in patients suffering from COPD (Bu et al. Chin Med J 2003; 116(3):459-461).

Even if there are no compelling clinical data for an additional contribution by $LTB_4$ in human asthma, in other respiratory conditions such as COPD, which are characterised by pronounced neutrophil infiltration, it may be that the chemotactic properties of $LTB_4$ are more important (Daniel and O'Byrne, Am Rev Respir Dis 1991; 143:S3-5). In patients suffering from COPD, the enhanced oxidative stress is paralleled by the increased ability of neutrophils to synthesize the chemotactic factor $LTB_4$, and may ultimately contribute to the infiltration/activation of neutrophils into the airways of COPD patients (Santus et al. Am J Respir Crit Care Med 2004; [Epub ahead of print]). Additionally, there is a selective increase in exhaled $LTB_4$ in patients with COPD (Montuschi et al. Thorax 2003; 58:585-8).

Anticholinergic medications have been accepted as an important treatment modality in diseases of the upper and lower airways, rhinitis, asthma and COPD. The muscarinic receptor antagonist, used in this invention will be a long-acting compound. Any compound of this type can be used in this combination therapy approach.

Glycopyrrolate, another quaternary ammonium anticholinergic compound, consists of four stereoisomers. Glycopyrrolate belongs to the so-called anticholinergic drugs and antagonizes the neurotransmitter acetylcholine at its receptor site. This effect leads to a considerable bronchodilatation and a reduced mucus secretion. It is poorly absorbed from mucus membranes, thus reducing anticholinergic side effects (Ali-Melkkila et al. Acta Anaesthesiol Scand 1993; 37:63342). Glycopyrrolate possesses no selectivity in As binding to the $M_1$-$M_3$ receptors. Kinetics studies, however, showed that glycopyrrolate dissociates slowly from $M_3$ muscarinic receptors (Haddad et al. Br J Pharmacol 1999; 127:413-20). Similarly to tiotropium, this behavior explains glycopyrrolate's relative receptor selectivity and its long duration of action. Indeed, there is evidence that racemic glycopyrrolate produces considerable and long-lasting bronchodilatory effects both in asthmatic and in COPD patients (Walker et al. Chest 1987; 91:49-51, Schroeckenstein et al. J Allergy Clin Immunol 1988I; 82:115-9, Gilman et al. Chest 1990; 98:1095-8, Cydulka and Emerman, Ann Emerg Med 1995; 25:470-3).

Additionally, the use of a topical anticholinergic medication (e.g. ipratropium or glycopyrrolate) in allergic rhinitis is both safe and effective in reducing the symptoms (Milford et al. J Laryngol Otol 1990; 104:123-5, Meltzer J Allergy Clin Immunol 1992; 90:1055-64). As rhinitis, asthma and COPD are characterized by increased mucus secretions, the antisecretory effect of anticholinergics such as glycopyrrolate is an additional advantage for their use in the therapy of these diseases.

DESCRIPTION OF THE INVENTION

Current treatments for asthma and COPD are not satisfactory. The same is valid for rhinitis where the relatively simple nasal disease, in spite of an apparently satisfactory treatment, further develops to a bronchial asthma. Given the high prevalence of these diseases, Therefore the problem underlying the present invention was the presentation of improved, more effective and more convenient therapeutic interventions.

This problem can be solved according to the invention by a combination of a topical anticholinergic with at least one leukotriene receptor-antagonist.

Antagonists of BLT- and CysLT-receptors reduce the inflammatory processes both in upper and lower airways (e.g. rhinitis, asthma and COPD). Thus, these effects of LT-receptor-antagonists result in an improved mucosal and bronchial function in patients suffering from airway diseases including allergic rhinitis, bronchial asthma or COPD. The pharmacodynamic properties of both drug classes, anticholinergics (especially R,R-glycopyrrolate) and LT-receptor-antagonists complement one another and result in more efficacious treatment of the mentioned diseases resulting in a minimization of systemic exposure. The combination according to the invention, LT-receptor antagonist and anticholinergic, is superior to monocompounds with respect to therapeutic efficacy, safety onset and duration of action, or side-effects, namely surprisingly in an overadditive manner. Additionally, the patients' compliance is also increased.

Experimental Part

Not only TNFα but also IL-2 plays an important role in inflammatory airway diseases. It is known that in certain forms of asthma (e.g. intrinsic and occupational), particular subsets of T cells produce, among others, IL-2 (Ricci et al.; J Investig Allergol Clin Immunol 1994; 4:214-20). Moreover, allergic patients have special populations of T cells which can be induced to secrete IL-2 (McHugh et al.; Clin Exp Allergy 1993; 23:137-44). It has also been demonstrated that zafirlukast, a cysLT-receptor antagonist was able to decrease, among others, the IL-2 expression in ovalbumin-sensitized Brown Norway rats (Lin et al.; Clin Exp Allergy 2002; 32:960-6). Therefore, the influence of R,R-glycopyrrolate in combination with cysLT-receptor antagonists on TNFα- and interleukin(IL)-2-release was investigated by using human peripheral blood mononuclear cells (PBMCs). The investigations were approved by the University Ethics Committee according to the International Declarations of Helsinki and Tokyo.

PBMCs were isolated from heparinized blood samples of healthy donors by density gradient centrifugation. An equal volume of Hanks buffer (Life Technologies, Heidelberg, Germany) is added to heparinized whole blood samples. 15 ml Histopaque-1077 (Sigma, Deisenhofen, Germany) are overlayed with a maximum of 40 ml of blood/Hanks mixture were centrifuged for 30 min at room temperature (2000 rpm). A visible band containing PBMCs is transferred to a fresh tube and washed twice with Hanks-buffer. Finally cells are seeded in RPMI 1640 Medium (Life Technologies, Heidelberg, Germany) with Glutamax I (Gibco BRL, Eggenstein) and 10% FCS (Boehringer Mannheim, Penzberg, Germany). After isolated, PBMCs were cultured in RPMI 1640 medium supplemented with 10% fetal calf serum (FCS) at 37° C. 5% $CO_2$ overnight. Monocytes were isolated from other cells by adherence method, non-adherent cells were removed by changing the medium.

Cells are re-suspended at $10^6$ cells/ml and incubated in 500 μl volumes in 24-well tissue culture plates (Falcon Becton Dickinson Labware) at 37° C., 5% $CO_2$. After pre-incubation with test substances (0.5 μl/500 μl medium) for 30 min, cells were stimulated with lipopolysaccharide (LPS) (100 ng/ml). Instead of LPS, TPA (phorbol-12-myristate-13-acetate) (25 nM) and ionomycine (1 μg/ml) were used to stimulate IL-2 release. At indicated times cells were sedimented by centrifugation. The supernatants were harvested and kept frozen at −80° C. until protein determination; the cells were lysed by RLT lysis Buffer (Qiagen, Hilden, Germany) and frozen at −80° C. until analysis.

Cytokine measurements in culture supernatants were done by sandwich ELISA using matched antibody pairs (Pharmingen, Heidelberg, Germany). ELISA plates (Maxisorb, Nunc) are coated overnight with anti-cytokine monoclonal antibody (mAb) in 0.1 M carbonate buffer, pH 9.5. After being washed, plates are blocked with Assay Diluent (Pharmingen, Heidelberg, Germany) for 1 h and washed again. Appropriately diluted supernatant samples and standards are distributed in duplicates and the plates are incubated for 2 h at room temperature. Plates are washed, incubated for 1 h with working detector (biotinylated anti-cytokine antibody and Avidin-horseradish peroxidase conjugate). After washing, substrate (TMB and hydrogen peroxide) is added. The reaction is stopped by adding of 1M $H_3PO_4$. Plates are read at 450 nm (reference 570 nm) in a microplate reader (Dynatech). The results are expressed as a percentage of the control level of cytokines production by cells stimulated in the absence of the compound.

Upon LPS-stimulation, basal TNFα release from monocytes increased from 150 pg/ml up to 3,208 pg/ml. R,R-glycopyrrolate alone did not influence the LPS-induced TNFα release up to 10 μmol/l. TPA/ionomycin considerably stimulated IL-2 release from PBMCs (from 0 pg/ml [under detection limit] up to 5,300 pg/ml). Similarly to TNFα, R,R-glycopyrrolate alone had no influence on the stimulated IL-2 release up to 10 μmol/l.

The cysLT-receptor antagonist montelukast inhibited the TNFα release in a concentration-dependent manner. The $IC_{50}$ value of montelukast amounted to 2.45±0.85 nmol/l. The simultaneous addition of 10 μmol/l of R,R-glycopyrrolate did not influence montelukast's $IC_{50}$ (2.58 nmo/l).

Montelukast significantly inhibited the IL-2 release with an $IC_{50}$-value of 0.88±0.14 nmol/l. The simultaneous addition of 10 μmo/l of R,R-glycopyrrolate surprisingly and highly significantly reduced the $IC_{50}$ to 0.26±0.07 nmol/l (p=0.0023) in an over-additive manner.

In summary, based on the present experimental investigations, we conclude that R,R-glycopyrrolate may significantly enhance the anti-inflammatory activity of cysLT-receptor antagonists.

EXAMPLES

The combination therapy contemplated by this invention comprises administering at least one cysLT-BLT-receptor antagonist with a long-acting anticholinergic compound to prevent onset of an upper or lower airway disease event or to treat an existing condition and to reduce airway inflammation. The compounds may be administered together in a single dosage form. Or they may be administered in different dosage forms. They may be administered at the same time. Or they may be administered either close in time or remotely, such as where one drug is administered in the morning and the second drug is administered in the evening. The combination may be used prophylactically or after the onset of symptoms has occurred. In some instances the combination(s) may be used to prevent the progression of an airway disease or to arrest the decline of a function such as lung function.

These drugs, the anticholinergics and the LT-receptor antagonists, are usually administered as an aerosol, or as an inhaled powder. This invention contemplates either administering one drug after the other or co-administering both drugs in one delivery form such as an inhaler, which is putting both drugs in the same inhaler in one or even more containers. Formulations are within the skill of the art. To date, all known LT-receptor antagonists are orally bioavailable and will be administered as tablets. However, there is evidence that LT-receptor antagonists are also effective when they are given topically. The potential role of the LT-receptor antagonist L-648,051 for local aerosol therapy for asthma is promising (Young Agents Actions 1988; 23(Suppl):113-9). The LT-receptor antagonist MK-571 completely inhibited in vivo chemotactic response in the guinea pig conjunctiva indicating the usefulness not only in allergic conjunctivitis but also in allergic rhinitis and asthma (Chan Eur J Pharmacol 1990; 191:273-80). Inhaled LT-receptor antagonist ICI 204,219 protected significantly against exercise-induced bronchoconstriction in asthmatic subjects (Makker Am Rev Respir Dis 1993; 147:1413-8). Inhaled LT-receptor antagonist verlukast (MK-0679) caused significant improvement in mean $FEV_1$ in asthmatic subjects (Lammers, Pulm Pharmacol 1992; 5:121-5). Inhaled LT-receptor antagonist AS-35 suppressed dose-dependently antigen induced bronchoconstriction in ventilated guinea pigs (Bando, Arzneimittelforschung 1994; 44:754-7). Inhaled LT-receptor antagonist pobilukast (SK&F 104353) inhibited significantly LT induced bronchoconstriction in asthmatic subjects (Christie, J Allergy Clin Immunol 1991; 88:193-8). Thus, inhaled LT-receptor antagonists like L-648,051 are suited for inhaled treatment (Evans, Br J Clin Pharmacol 1989; 28: 125-35).

Zafirlukast administered topically into the eyes effectively inhibit the development of symptoms and mediator release in an experimental model of allergic conjunctivitis in rats (Papathanassiou et al. lnflamm Res 2004; 53:373-6).

The active ingredients may be given from 1 to 8 times a day, sufficient to exhibit the desired activity. Preferably, the active components are given about once or four times a day, more preferably once or twice a day. The long duration of action makes twice daily administration possible. If the active components are present in the form of a fixed combination, administration is simpler for the patient, because both active ingredients are contained in one device.

The LT-receptor antagonist, for example montelukast can be orally administered in an amount of between 1 and 100 mg/day adult human with the preference of 5 to 20 mg/day in dependence of the intensity of the airway inflammation. In nasal sprays or drops the concentration of the LT receptor antagonists, for example montelukast, in the combination can be in the range from 0.01 to 5%. Preferred concentrations are 0.1% to 2% for the LT receptor antagonist. In metered dose inhalers or dry powders for inhalation the dose of the LT receptor antagonists, for example montelukast, in the combination can be in the range from 0.05 to 10 mg per dose, preferentially 0.2 to 5 mg per dose.

The inhaled anticholinergic drug, for example racemic glycopyrrolate, one of its enantiomers, especially R,R-glycopyrrolate or a mixture thereof and its salt, solvates and hydrates can be administered from a metered dose inhaler or a dry powder for inhalation in an amount of between 1 and 500 µg/day adult human with the preference of 5 to 100 µg/day. In nasal sprays or drops the concentration of the anticholinergic components, e.g. glycopyrrolate, according to the present invention can be in the range from 0.0001% to 0.5%. Preferred concentrations are 0.001 to 0.1% for R,R-glycopyrrolate.

It is contemplated that both active agents would be administered at the same time, or very close in time. Alternatively, one drug could be taken in the morning and one later in the day. Or in another scenario, one drug could be taken twice daily and the other once daily, either at the same time as one of the twice-a-day dosing occurred, or separately. Preferably both drugs would be taken together at the same time.

For the veterinary use, the anticholinergic, e.g. glycopyrrolate, can be given to horses in an amount of 1 to 32 µg/kg/day with the preference between 4 and 16 µg/kg/day alone or in combination with an inhaled or orally administered LT-receptor antagonist. The cysLT-receptor antagonist, for example montelukast can be administered in an amount of between 10 and 1,000 mg/day horse with the preference of 50 to 200 mg/day in dependence of the intensity of the airway inflammation. The desired dose for a BLT-receptor antagonist depends on its receptor affinity and availability at the receptor site.

Formulation and Process of Production

The present invention describes a combination in which a anticholinergic such as R,R-glycopyrrolate administered alone or in combination with an LT-receptor antagonist, e.g. montelukast, zafirlukast and/or pranlukast are administered simultaneously, one after the other as individual substance or as a fixed combination in the described matter.

The active substances can be given, according to the invention, simultaneously, successively or independently of one another, topically (intranasally or by inhalation) as a fixed combination or in individual substances or orally combined with topically. If separate formulations are present, then these are tailored to one another and contain the respective active compounds in the dosage unit in the same amounts and corresponding weight ratios in which they can be present in the combination.

The compositions of oral or topical administration can be formulated as different, pharmaceutically acceptable forms of administration, e.g. nasal sprays or nasal drops, tablets, film coated tablets, capsules or granules. The topical dosage forms may also include an emulsion, a paste, a cream and/or a gel.

In addition to the active compounds the pharmaceutical preparations according to the invention can contain further constituents such as preservatives, stabilizers, isotonicizing agents, thickeners, suspension stabilizers, excipients for pH adjustment, buffer systems, wetting agents and others, e.g. colorants.

Antimicrobial preservative substances include, for example: benzalkonium chloride, chlorobutanol, thiomersal, methylparaben, propylparabe, sorbic acid and it salts, sodium edetate, phenylethyl alcohol, chlorhexidine hydrochloride and bromide, chorhexidine acetate, chlorhexidine digluconate, chlorocresol, phenylmercury salts, phenoxyethyl alcohol, cetylpyridinium chloride or bromide.

A combination of sodium edetate and benzalconium chloride can be suitable used as a preservative. Sodium edetate is used in concentrations of from 0.05 to 0.1%, and benzalkonium chloride in concentrations of from 0.005 to 0.05% wt., based on the composition.

Suitable excipients for the adjustment of the isotonicity or osmolarity of the formulations are, for example: sodium chloride, potassium chloride, mannitol, glucose, sorbitol, glycerol, propylene glycol. In general, these excipients are employed in concentrations from 0.1 to 10%.

The formulations of the invention can also include suitable buffer systems or other excipients for pH adjustment in order to establish and maintain a pH of the order of magnitude of 4 to 8, preferably of 5 to 7.5. Suitable buffer systems are for example citrate, phosphate, tromethamol, glycine, borate, acetate. These buffer systems can be prepared from substances such as, citric acid, monsodium phosphate, disodium phosphate, glycine, boric acid, sodium tetraborate, acetic acid, sodium acetate. Further excipients can also be used for pH adjustment, such as hydrochloric acid or sodium hydroxide.

In order to prepare a stable aqueous suspension containing a water-insoluble active compound, suitable suspension stabilizers and suitable wetting agents are furthermore necessary in order to disperse and to stabilize the suspended drug substance in a suitable manner.

Suitable suspension stabilizers are water-soluble or partly water-soluble polymers: these include, for example, methylcellulose (MC), sodium carboxymethylcellulose (Na-CMC), hydroxypropylmethylcellulose (HPMC), polyvinyl alcohol (PVAL), polyvinylpyrrolidone (PVP), polyacrylic acid, polyacrylamide, gellan gum (Gelrite®), hydrated alumina (Unemul®), dextrins, cyclodextrins, cellulose acetate phtalate, and mixtures of microcristalline cellulose (different types of Avicel®) and sodium carboxymethylcellulose. These substances can simultaneously serve as thickeners in order to increase the viscosity and thereby to prolong the contact of the drug substances with the tissue at the application site.

Suitable wetting agents are, for example: benzalkonium chloride, cetylpyridinum chloride, tyloxapol, various polysorbates (Tween®), and further polyethoxylated substances and poloxamers.

For nasal administration of solutions or suspensions according to the invention, various devices are available in the art for the generation of drops, droplets and sprays. For example, formulations can be administrated into the nasal passages by means of a dropper (or pipette) that includes a glass, plastic or metal dispensing tube. Fine droplets and sprays can be provided by an intranasal pump dispenser or squeeze bottle as well known to the art.

The invention also includes a kit containing one or more unit dehydrated doses of one or more drug substances as well as any required excipients of the formulation, ready for preparation of a solution or suspension by addition of a suitable amount of sterile or nonsterile water.

The active substances can be given, according to the invention, simultaneously, successively or independently of one another, by inhalation as a fixed combination or in individual substances or orally combined with inhalation.

As inhalable compositions pressurized metered dose inhalers, dry powders or inhalation solutions without propellant can be considered. Among the latter are even sterile, ready for use or just before use manufactured inhalation solutions, suspensions or concentrates as a nebulizable composition in an aqueous and/or organic medium. These dosage forms are part of the present invention.

Pressurized metered dose inhalers with propellants may contain the active R,R-glycopyrrolate and at least one LT-receptor antagonist in solution or in dispersion in a propellant. The propellants which can be used for inhalation aerosols in this invention are well known: mainly halogenated hydrocarbon derivatives, TG134a and TG227, or their mixtures are applied. Furthermore detergents (eg. oleic acid), stabilizers (eg. sodium edetate), co-solvents (eg. propyleneglycol, polyethyleneglycol, glycerol), antioxidants (eg. ascorbic acid), lubricants (eg. polyoxyethylene-glyceryl-trioleate) or buffer systems or other excipients for pH adjustment (eg. hydrochloric acid) are normally added. The active ingredient may have an average particle diameter of up to 5 μm.

A combination of ethyl alcohol and polyoxyethylene-25-glyceryi-trioleate (trade name: Tagat TO) can be suitable used as a detergent/stabilizer/co-solvent/lubricant complex in a concentration between 0.5 and 1.5%.

The above mentioned aerosols containing a propellant, solutions or suspensions according to the invention are administered by state of the art inhalers, so-called pressurized metered dose inhalers (=pMDI). They can be equipped with different-sized metal or plastic stems responsible for metering and release of the actives.

Dry powders contain the active anticholinergic and/or at least one LT-receptor antagonist either alone or in a mixture with a pharmaceutically suitable, physiologically harmless carrier. This can be chosen from materials known as carriers in dry powder inhalation compositions for example monosaccharides (eg. glucose, arabinose), disaccharides (eg. lactose, saccharose, maltose), oligo- and polysaccharides (eg. dextran) and sugar alcohols (eg. sorbit, mannit).

Best available technology is to use mainly lactose as lactose monohydrate. The used excipients feature a particle size distribution up to approximately 500 μm, the preferred mean particle diameter is approximately 110 to 290 μm. The active ingredient may have an average particle diameter of up to 4 μm.

The inhalation powders according to this invention can be administered by the help of state of the art dry powder inhalation devices for instance the Novolizer®. The inhalation powder can be pre-metered in capsules (eg. gelatine) or blisters (aluminium pouches) or metered just before use from a bulk reservoir. The anticholinergic and at least one LT-receptor antagonist can be there in a fixed combination or both actives are in separate packaging units, that they can be administered independent of each other from one device or a pack from two or more different devices or simultaneously.

The following examples shall illustrate the invention without restricting it.

Example 1

| Nasal spray or nasal drops containing glycopyrrolate | |
|---|---|
| R,R- Glycopyrrolate | 0.0070 g |
| Hydroxypropylmethylcellulose | 0.1000 g |
| Sodium edetate | 0.0500 g |
| Benzalkonium chloride | 0.0125 g |
| Sorbitol solution 70% | 6.6000 g |
| Purified water | to 100 ml |

Preparation of the Solution

Introduce 80% of purified water into a suitable stirrer-equipped container. Add the Glycopyrrolate, Hydroxypropylmethylcellulose, Benzalkonium chloride, Sodium edetate and Sorbitol solution successively thereto and dissolve with stirring. Make up to the final volume using purified water and stir. Filter the solution through a membrane filter having a pore size of 0.2 μm and dispense into bottles.

Example 2

| Nasal spray or nasal drop suspension containing montelukast (1%) | |
|---|---|
| Montelukast | 1.0000 g |
| Avicel RC 591 | 1.1000 g |
| Polysorbate 80 | 0.1000 g |
| Sodium edetate | 0.0500 g |
| Benzalkonium chloride | 0.0200 g |
| Sorbitol solution 70% | 6.0000 g |
| Purified water | to 100 ml |

Preparation of the Suspension:

Introduce 80% of purified water into a suitable stirrer-equipped container having a homogenizing device and homogenize Avicel RC 591 therein at high speed. Then dissolve the substances Polysorbate 80, sorbitol solution, sodium edetate and benzalkonium chloride with stirring. Then homogenize in the active compound montelukast at high speed until a uniform suspension results. Then make up to the final volume with purified water and homogenize further. Then evacuate the suspension in order to remove the resulting air bubbles. The resulting suspension is then dispensed into bottles.

Example 3

| Nasal spray or nasal drops comprising R,R- Glycopyrrolat and montelukast | |
|---|---|
| R;R- Glycopyrrolat | 0.0070 g |
| Montelukast | 1.0000 g |
| Avicel RC 591 | 1.1000 g |
| Polysorbate 80 | 0.1000 g |
| Sodium edetate | 0.0500 g |
| Benzalkonium chloride | 0.0200 g |
| Sorbitol solution 70% | 6.0000 g |
| Purified water | to 100 ml |

Preparation:

Introduce 80% of purified water into a suitable stirrer-equipped container having a homogenizing device and homogenize Avicel RC 591 therein at high speed. Then dissolve the R,R-Glycopyrrolate and the excipients Polysorbate 80, sorbitol solution, sodium edetate and benzalkonium chloride with stirring. Then homogenize in the active compound montelukast at high speed until a uniform suspension results. Then make up to the final volume with purified water and homogenize further. Then evacuate the suspension in order to remove the resulting air bubbles. The resulting suspension is then dispensed into bottles.

Example 4

| Dry Powder for Inhalation with 20 μg glycopyrrolate and 2.5 mg Montelukast per single dose | |
|---|---|
| R;R- Glycopyrrolat | 20.000 g |
| Montelukast | 2500.000 g |
| Lactose | 9480.000 g |

Preparation of a Dry Powder for Inhalation:

A quantity of 20 g micronized glycopyrrolate is mixed with 180 g alpha lactose monohydrate, the mixture is given on a sieve of 0.5 mm mesh size and finally mixed again. The mixture received is mixed with 1800 g alpha lactose monohydrate (=mixture 2). This mixture is divided into two parts. The first part of the glycopyrrolate/lactose mixture 2 and 2,500 g micronized Montelukast are blended, the mixture is given on a sieve of 0.8 mm mesh size and finally mixed again (=mixture 3). Mixture 3 and 7,500 g lactose are blended first; finally this mixture and the second part of the glycopyrrolate/lactose mixture 2 are blended (=mixture 4). The received mixture is given on a sieve of 0.8 mm mesh size. Subsequently, it is mixed again and the powder mixture received is filled in powder inhalers releasing 12 mg of powder per single dose.

Per single dose, 20 μg glycopyrrolate and 2.5 mg Montelukast are released from a powder inhaler and supplied to the patient's airways.

Example 5

| Pressurized metered dose inhaler with 50 μg glycopyrrolate and 2.5 mg Montelukast per single dose | |
|---|---|
| R;R- Glycopyrrolat | 0.840 g |
| Montelukast | 42.000 g |
| Saccharin Sodium | 1.800 g |
| Tagat TO | 23.400 g |
| Absolute Ethyl alcohol | 23.400 g |
| HFA 227 | ad 2340.000 g |

Preparation of the Pressurized Metered Dose Inhaler:

A quantity of 2000 g 1,1,1,2,3,3,3, heptafluoropropane (=HFA) 227) is cooled down at a temperature of −55° C. and, while stirring, mixed up with a solution of 23.4 g polyoxyethylene-25-glyceryl-trioleate (trade name: Tagat TO) in 23.4 g absolute ethyl alcohol.

Subsequently, 0.840 g micronised glycopyrrolate and 42.000 g micronised Montelukast as well as 1.800 g micronised saccharin sodium is added, and the suspension produced is intensively homogenized. While further cooling and stirring, the suspension is filled up with refrigerated propellant 227 to 2340 g and after mixing again filled in metal cans which are closed with metering valves releasing 100 μl of the suspension per actuation.

50 μg glycopyrrolate and 2.5 mg Montelukast are released per actuation.

We claim:

1. Combination of R,R-glycopyrrolate or a physiologically acceptable salt thereof and montelukast or a physiologically acceptable salt thereof for the treatment of respiratory diseases selected from the group consisting of allergic rhinitis, bronchial asthma, and COPD to provide a daily dose of montelukast from 1 to 100 mg, and a daily dose of R,R-glycopyrrolate from 1 to 500 µg.

2. Combination according to claim 1 where the daily dose of montelukast is from 5 to 20 mg.

3. The combination according to claim 1 wherein the daily dose of R,R-glycopyrrolate is from 5 to 100 µg.

4. A pharmaceutical for the treatment of respiratory diseases selected from the group consisting of allergic rhinitis, bronchial asthma, and COPD, comprising R,R-glycopyrrolate or a physiologically acceptable salt thereof and montelukast or a physiologically acceptable salt thereof to provide a daily dose of montelukast from 1 to 100 mg, and a daily dose of R,R-glycopyrrolate is from 1 to 500 µg.

5. The pharmaceutical according to claim 4, where the active substances are available readily mixed in a fixed combination, if appropriate together with excipients, adjuncts, and additives in a pharmaceutical form suitable for inhalative application.

6. The pharmaceutical according to claim 4, wherein the active substances are available in separate packing units whereby both substances can be taken from the separate packing units in such a way that they are available for simultaneous inhalative application.

7. The pharmaceutical according to claim 6, wherein the active substances can be applied independently from each other.

8. The pharmaceutical according to claim 5, characterized in that it is an inhalable aerosol with or without propellant.

9. The pharmaceutical according to claim 5, characterized in that it is an inhalable dry powder.

10. The pharmaceutical according to claim 5, characterized in that it is an inhalable suspension or solution.

11. The pharmaceutical according to claim 5 presented in an inhaler.

12. A method of making a pharmaceutical according to claim 4 for the treatment of respiratory diseases selected from the group consisting of allergic rhinitis, bronchial asthma, and COPD in a mammal, said method comprising combining R,R-glycopyrrolate or a physiologically acceptable salt thereof and montelukast or a physiologically acceptable salt thereof.

13. The method according to claim 12 wherein the mammal is selected from the group consisting of cats, dogs, or horses.

14. The method according to claim 12 wherein the diseases are selected from the group consisting of asthma and chronic obstructive pulmonary disease (COPD).

15. A method of treating inflammation associated with a respiratory disease selected from the group consisting of allergic rhinitis, bronchial asthma, and COPD in a mammal in need thereof comprising administering a daily dose of R,R-glycopyrrolate or a physiologically acceptable salt thereof in an amount of from 1 to 500 µg and a daily dose of montelukast or a physiologically acceptable salt thereof in an amount of from 1 to 100 mg to said mammal in dosages thereby reducing inflammation associated with the respiratory disease.

16. The method according to claim 15 characterized in that the mammal is selected from the group consisting of cats, dogs, or horses.

17. The method according to claim 15 where the diseases are selected from the group consisting of asthma and chronic obstructive pulmonary disease (COPD).

* * * * *